United States Patent [19]

Cioppi

[11] Patent Number: 4,775,237

[45] Date of Patent: Oct. 4, 1988

[54] ELECTRO-OPTICAL DETECTION SYSTEM

[75] Inventor: Joseph A. Cioppi, Hatboro, Pa.

[73] Assignee: Innovative Medical Systems Corp., Ivyland, Pa.

[21] Appl. No.: 25,986

[22] Filed: Mar. 16, 1987

[51] Int. Cl.$^4$ .......................................... G01N 21/64
[52] U.S. Cl. ................................ 356/417; 250/458.1; 356/317
[58] Field of Search ............... 356/317, 318, 319, 323, 356/325, 326, 328, 417; 250/458.1, 459.1, 461.1, 461.2

[56]  References Cited

U.S. PATENT DOCUMENTS

| | | | |
|---|---|---|---|
| 3,897,155 | 7/1975 | Smythe | 356/317 |
| 3,985,442 | 10/1976 | Smith et al. | 356/326 |
| 4,201,472 | 5/1980 | Maeda | 356/226 |
| 4,412,744 | 11/1983 | Lee et al. | 356/319 |
| 4,451,149 | 5/1984 | Noeller | 356/317 |

FOREIGN PATENT DOCUMENTS 0046887  4/1977  Japan ................................. 356/319

Primary Examiner—F. L. Evans
Attorney, Agent, or Firm—Robert J. Mooney; Armand M. Vozzo, Jr.

[57] ABSTRACT

An improved electro-optical detection system is disclosed capable of use in a fluorescent polarization instrument. In a single or dual channel system, an integrated photodetector/amplifier is combined with a linear charge-balancing voltage-to-frequency converter to produce a digital frequency indicative of the intensity of polarized fluorescence emmited by a chemically treated body fluid sample, such as blood, upon light excitation thereof. A chopper-stabilized amplifier is further connected to the input of the voltage-to-frequency converter for automatically correcting input offset currents and temperature drift. The digital frequency is counted and the data corresponding thereto is transferred via bus connection to a microcomputer for evaluation and display.

18 Claims, 2 Drawing Sheets

ELECTRO-OPTICAL DETECTION SYSTEM

BACKGROUND OF THE INVENTION

The present invention relates to fluorescence polarization instruments of the type typically used to analyze body fluid samples treated with fluorescent materials and more particularly, to an improved electro-optical detection system for producing digitally compatible data signals indicative of fluorescence levels emitted from such samples for more effective computerized analysis thereof.

In the field of analytical chemistry, fluorescence polarization instruments are well known for their use in clinical applications. Particularly useful in medical laboratories, such instruments can rapidly analyze body fluid samples, such as those of a patient's blood, which have been treated with a fluorescent material in order to determine the presence and molar concentration of selected substances in the samples.

Generally, these fluorescent polarization instruments operate so as to direct one or more beams of linearly polarized excitation light upon the treated sample. The excitation light is typically of a high intensity and monochromatic corresponding to the peak of the absorption spectrum of the sample. The fluorescent molecules, when excited by the polarized light, emit luminous energy which, in its polarization value, decisively depends upon the molecular size of the species which fluoresces. The degeee of polarization also depends upon other parameters, such as, for example, the number of type of these molecules, the state of the molecules, i.e. whether or not the molecules are bound or unbound to one another.

The illuminated fluorescent sample therefore becomes a secondary source of radiation, emitting light in a spectrum peaked at a somewhat longer wavelength than the excitation light. A vertical polarizer in the emission light path passes vertically polarized light to a photosensor for detecting the resulting emission light from the sample and measuring the intensity of the fluorescent emission. A second polarizer in a separate emission light path passes horizontally polarized light from the radiating fluorescent sample to a second photosensor to simultaneously measure the horizontal component of a fluorescent emission and permit a complete and accurate determination of the degree of polarization of the emitted light.

In the detection and conversion circuitry, existing fluorescent polarization instruments have generally utilized photosensors, the current outputs of which have been amplified and converted to meaningful measurement signals using typical analog methods. The dynamic range and linearity, however, of these instruments has been limited due to inadequacies of the analog system in signal amplification and conversion. Furthermore, such analog conversion systems have been less than satisfactory in operating over a wide range of emission light intensities, particularly at lower intensity levels. While some designs heretofore developed for analog-to-digital conversion have increase accuracy and resolution of the fluorescence measurements, such designs have been expensive and somewhat difficult to produce.

SUMMARY OF THE INVENTION

Accordingly, it is a general purpose and object of the present invention to provide an improved fluorescence polarization instrument capable of analyzing body fluid samples, such as those of human blood, with greater reliability and accuracy than those instruments produced heretofore.

It is a more particular object of the present invention to provide an improved electro-optical means for detecting changes in the intensity of light emissions, polarized or non-polarized, from a chemically treated body fluid sample being analyzed and producing data signals indicative thereof for digital compatibility with computerized measuring equipment.

It is a further object of the present invention to provide an electro-optical detection system capable of use in a fluorescence polarization instrument that increases the dynamic range and linearity of light intensity measurements while maintaining a high level of accuracy and resolution.

It is a still further object of the present invention to provide an electro-optical detection system that is virtually drift-free requiring minimum alignment adjustments, inexpensive to manufacture, and readily adapted to existing instrument systems, particularly those computerized.

Briefly, these and other objects of the present invention are accomplished by an improved electro-optical detection system for particular use in a fluorescent polarization instrument. In a single or dual channel system, an integrated photodetector/amplifier is combined with a linear charge-balancing voltage-to-frequency converter to produce a digital frequency indicative of the intensity of polarized fluorescence emitted by a chemically treated body fluid sample, such as blood, upon light excitation thereof. A chopper-stabilized amplifier is further connected to the input of the voltage-to-frequency converter for automatically correcting input offset currents and temperature drift. The digital frequency is counted and the data corresponding thereto is transferred via bus connection to a microcomputer for evaluation and display.

For a better understanding of these and other aspects of the present invention, reference may be made to the following detailed description taken in conjunction with the accompanying drawing in which like reference numerals and characters designate like elements throughout the figures thereof.

DESCRIPTION OF THE PREFERRED EMBODIMENT

Figure 1:
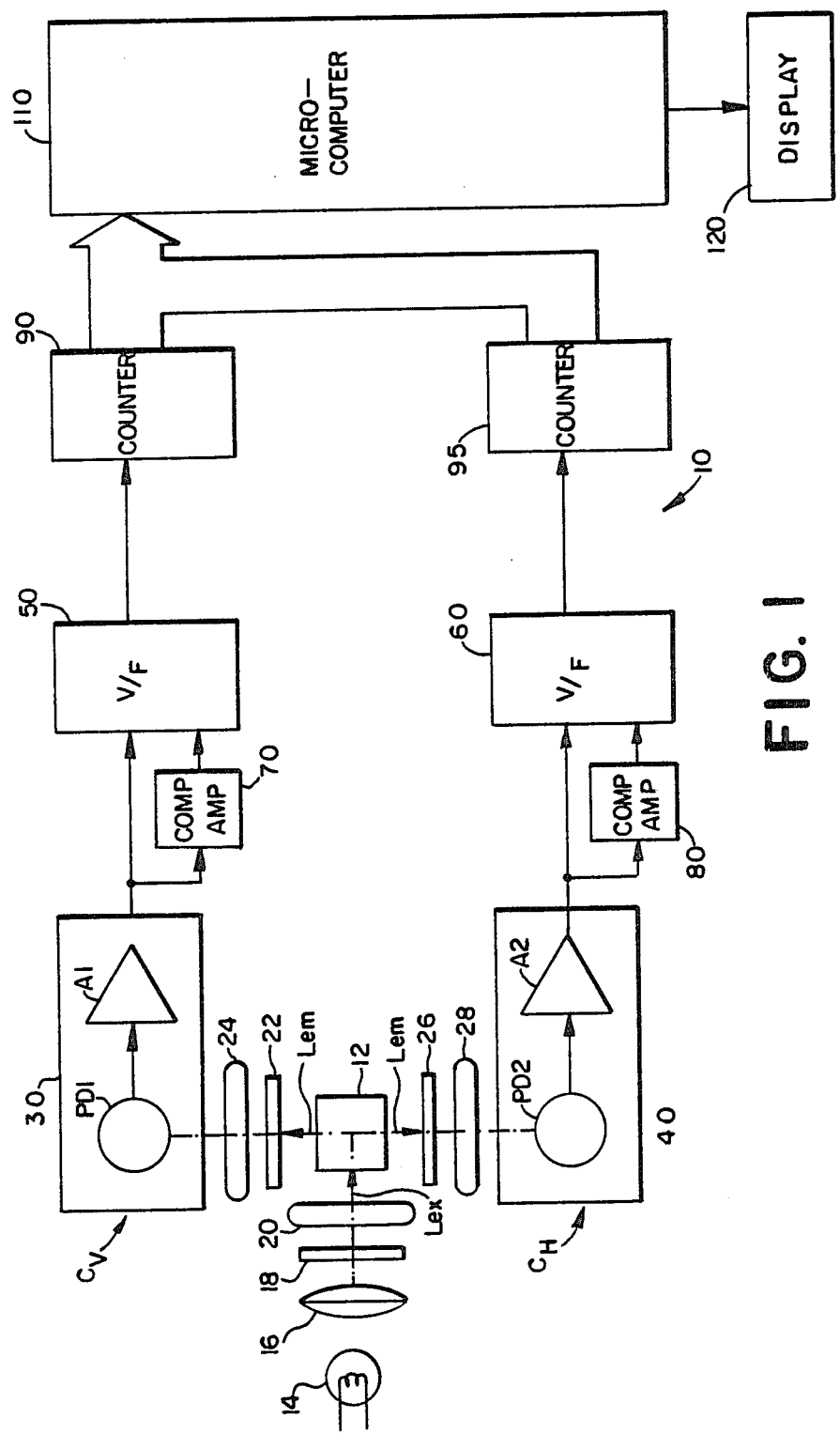
FIG. 1 is a block diagram of a fluorescence polarization instrument system incorporating the electro-optical detector system of the present invention.

Referring now to FIG. 1, there is shown a dual channel fluorescence polarization instrument system 10 used to determine the presence and molar concentration of selected substances in a body fluid sample, such as human blood. The sample is contained in a sample cell or cuvette 12 and is treated with a selected fluorescent dye material having a known absorption band of wavelengths, the selection of which is based upon the substance or substances being sought in the sample. The cuvette 12 with the sample contained therein is mounted within the system 10 so as to be directly exposed and receptive to a linearly polarized beam of excitation light $L_{ex}$ generated by a conventional broadband light source 14, such as a tungsten-halogen lamp. Intermediate of the light source 14 and the cuvette 12, a collimator lens 16 or group thereof collimates the incoming light from the source. The collimated light from lens 16 is passed through an optical filter 18 that limits the bandwidth of the light to correspond more nearly to the absorption peak of the selected fluorescent dye material. At the input to cuvette 12, for the purpose of exciting the sample contained therein, the filtered and collimated light is then passed through a film polarizer 20 oriented to produce the beam of excitation light $L_{ex}$ linearly polarized in a vertical direction.

At the output of cuvette 12, a set of optical elements are disposed on opposite sides of the cuvette substantially perpendicular to the incoming beam of excitation light $L_{ex}$ for receiving separate beams of a fluorescent emission light $L_{em}$ irradiated from the excited sample and transmitting respective vertically and horizontally polarized components thereof. A bandwidth filter 22 selected in accordance with the absorption spectrum of the particular fluorescent dye utilized and a film polarizer 24 oriented to pass vertically polarized light are arranged on one side of cuvette 12 in the path of emission light $L_{em}$. A filter 26 similar to bandwidth filter 22 and a horizontally oriented polarizer 28 are disposed at the opposite side of the cuvette 12.

Figure 2:
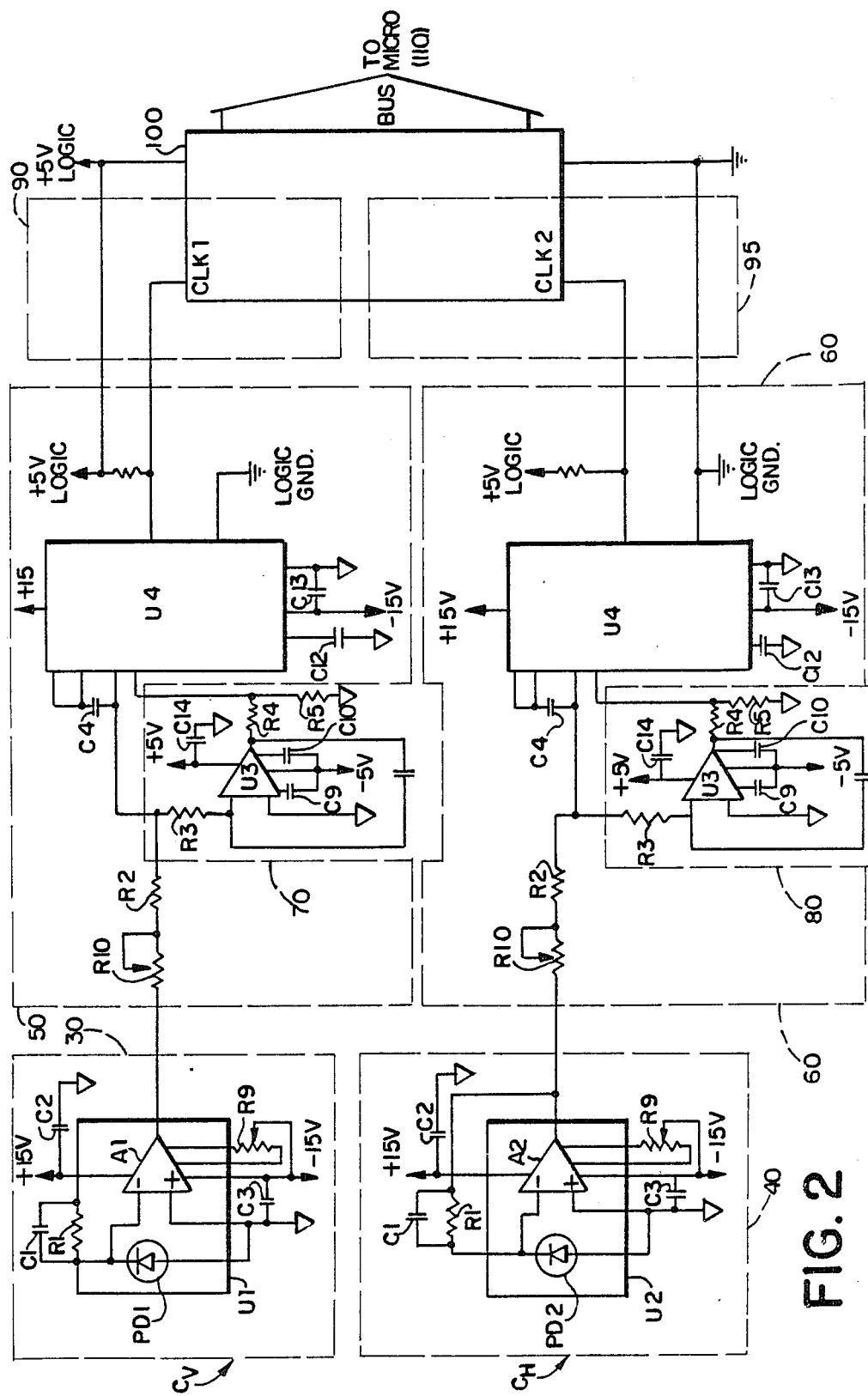
FIG. 2 is a detailed circuit diagram of the electro-optical detection system according to the present invention.

In the illustrated fluorescence polarization instrument system 10, a pair of identical electro-optical channels $C_V$ and $C_H$ are employed in accordance with the present invention for detecting the respective vertical and horizontal polarized components of emission light $L_{em}$ and producing digital data indicative of their intensities. Photodetector circuitry 30 and 40 in each channel $C_V$ and $C_H$ includes a respective photodiode PD1, PD2 and an associated operational amplifier A1, A2 connected to the output thereof. Mounted with their respective operational amplifiers A1 and A2 in an integral package U1 and U2, as shown in FIG. 2, the photodiodes PD1 and PD2 are each disposed in a position to directly receive the vertically and horizontally polarized beams of emission light $L_{em}$. Responsive to the intensity of each polarized beam of emission light $L_{em}$, the photodiodes PD1 and PD2 generate output currents that are both amplified and converted to an analog voltage signal by the associated operational amplifiers A1 and A2.

A voltage-to-frequency (V/F) converter circuit 50 and 60 is connected to the output of the respective photodetector circuitry 30 and 40 in each electro-optical channel $C_V$ and $C_H$. Each V/F converter circuit 50 and 60 is designed to convert the analog voltage signal received from the associated photodetector circuitry 30 and 40 into a digital frequency signal which directly corresponds to the level of light intensity of the respectively detected polarized beams of emission light $L_{em}$. V/F converter circuits 50 and 60 are each further provided with an input from a respective compensation amplifier circuit 70 and 80. These compensation amplifier circuits 70 and 80 each take the analog voltage signals produced by the respective photodetector circuitry 30 and 40 and employ chopper stabilization, as described hereinbelow in reference to FIG. 2, to automatically correct for input offset currents and temperature drifts affecting the analog voltage signals received by the V/F converter circuits 50 and 60. Accordingly, the V/F converter circuits 50 and 60 typically operate over 6 decades of input voltage signals without need for offset adjustment, thus converting to over 6 decades of light intensities ranging from 10 nanowatts ($10^{-8}$ W) to 0.1 picowatts ($10^{-13}$W) This allows each electro-optical channel $C_V$ and $C_H$ to track wide range variations in light input without gain adjustments and without the usual temperature drift associated with other detection systems requiring stepped or variable gain preamplifiers. Drift in the V/F converter circuits 50 and 60 using the respective chopper-stabilized compensation amplifiers 70 and 80 is typically 0.01 mv/° C.

The digital frequency signals produced by the V/F converter circuits 50 and 60 are delivered to an associated frequency counter 90 and 95 in each electro-optical channel $C_V$ and $C_H$. Each frequency counter 90 and 95 is designed to conventionally count the digital frequency output of the V/F converter circuits 50 and 60 as they are indicative of the light intensities of the differently polarized beams of emission light $L_{em}$, and transfer the data corresponding thereto to a conventional microcomputer 110 via a bus connection. In the dual channel system 10 illustrated herein, the frequency counters 90 and 95 may comprise a single counter timer 100, as shown in FIG. 2. The data thus produced from each electro-optical channel $C_V$ and $C_H$ is evaluated and processed by the micro-computer 110 and thereafter reported on a conventional display 120 to a user, such as a clinical medical operator, in the form of the molar concentrations of the sample.

Referring now to FIG. 2 in conjunction with FIG. 1, the component elements of the electro-optical channels $C_V$ and $C_H$ are shown in greater detail. Due to the identical nature of each channel $C_V$ and $C_H$, the analogous component elements thereof are similarly identified with the exception of the integral photodetector/amplifier packages U1 and U2 containing photodiodes PD1, PD2 and associated operational amplifiers A1, A2. One such integral photodetector/amplifier package U1, U2 suitable in the present invention is a Model UDT-020D manufactured by United Detector Technology.

The following is a list of the resistor and capacitor elements included in each electro-optical channel $C_V$ and $C_H$ along with examples of suitable values therefor:

|  | Suitable Values |
|---|---|
| Resistor elements | |
| R1 | 10 Meg.Ω, 5%, ¼ w |
| R2 | 14.3KΩ, 1%, ⅛ w |
| R3,R4 | 100KΩ, 1%, ⅛ w |
| R5 | 100Ω, 1%, ⅛ w |
| R6,R7 | 330Ω, 5%, ¼ w |
| R8 | 1KΩ, 5%, ¼ w |
| R9 | 100KΩ |
| R10 | 1KΩ |
| Capacitor Elements | |
| C1,C11 | 0.01 f, 50 v. |
| C2,C3,C5,C6,C13,C14 | 0.1 μf, 50 v. |
| C4 | 0.001 μf, 50 v. |
| C7,C8 | 33 μf, 25 v. |
| C9,C10 | 0.1 μf, 100 v. |
| C12 | 50 pf, 100 v. |

Each compensation amplifier circuit 70 and 80 includes an integrated operational amplifier U3 of a commercially available design that features a conventional operating technique called chopper stabilization. Chopper stabilization constantly corrects for errors in the offset voltage delivered to the operational amplifier U3 and otherwise accommodates random changes in the offset voltage due to time, temperature and common-mode voltage variations. Such chopper stabilization, which also diminishes low frequency noise affecting the respective amplifier circuits 70 and 80, is essentially performed by integral analog switching within each operational amplifier U3 controlled in conjunction with a pair of external capacitors, C9 and C10, which together operate to sample and hold in alternating cycles the offset correction voltage and the amplified input signal within each operational amplifier. Provided the switching between such alternating cycles is at a frequency substantially higher than the signal frequency, a continuous output signal is produced by each operational amplifier U3 and supplied to the V/F converter circuits 50 and 60 from respective compensation amplifier circuits 70 and 80. It should be noted that the internal switching of operational amplifiers U3 may be externally synchronized with a master system clock (not shown). One such operational amplifier U3 suitable for use in the compensation amplifier circuits 70 and 80 is that Model LTC-1052-CN8 manufactured by Linear Technology.

The V/F converter circuits 50 and 60 in each electro-optical channel $C_V$ and $C_H$ comprise essentially a commercially available integrated V/F converter chip U4 designed to operate in a highly linear fashion, converting analog input voltages into frequency pulses by means of a conventional operating technique called charge-balancing. This type of charge-balancing V/F converter U4 generally consists of an integral current source with controlled analog switching that permits the input signal current to be exactly balanced by an internal feedback current. The internal feedback is applied in short, accurately-timed bursts of current that are delivered per unit time as a linear function of the input signal amplitude, each burst of current being designed to produce one pulse from the converter's output stage. As a result the voltage-to-frequency transformation generated by this charge-balancing V/F converter U4 is highly linear. Input resistors R2 and R10 and a timing capacitor C12 determine that full-scale frequency of the V/F converter U4 and its input voltage range. A suitable V/F chip U4 for use in the converter circuit 50 and 60 is available from Analog Devices, Model No. AS650KN.

The use of the compensation amplifier circuits 70 and 80 in connection with the respective V/F converter circuits 50 and 60 effectively cancels any input offset on the input terminals of the V/F converter U4 by means of the continuous output signals provided by each operational amplifier U3. This combination of compensation circuits 70 and 80 and V/F converter circuits 50 and 60 thus improves the level of stability in the data signals produced by each electro-optical channel $C_V$ and $C_H$ as indicative of the respectively detected polarized beams of emission light $L_{em}$. Cancellation of the input offset also eliminates the need for any manual adjustment of the internal amplifier circuitry within the U/F converter U4 and allows the full 6 decade dynamic range of the converter to be utilized.

Therefore, it is apparent that the disclosed invention provides an improved fluorescence polarization instrument capable of analyzing body fluid samples, such as those of human blood, with greater reliability and accuracy than those instruments produced heretofore. More particularly, the disclosed invention provides an improved electro-optical means for detecting changes in the intensity of light emissions, polarized or non-polarized, from a chemically treated body fluid sample being analyzed and producing data signals indicative thereof for digital compatibility with computerized measuring equipment. The disclosed electro-optical detection system increases the dynamic range and linearity of light intensity measurements while maintaining a high level of accuracy and resolution. In addition, the present electro-optical detection system is virtually drift-free requiring minimum alignment adjustments, is inexpensive to manufacture and readily adapted to existing fluorescence polarization instruments, particularly those computerized.

Obviously, other embodiments and modifications of the present invention will readily come to those of ordinary skill in the art having the benefit of the teachings presented in the foregoing description and drawings. For example, a single electro-optical channel according to the present invention could be used to detect the light intensity of a single linearly polarized beam of emission light $L_{em}$, either vertically or horizontally, and then produce, in the aforedescribed manner, digital data indicative thereof for computerized processing. Furthermore, the described electro-optical channels, either individually or collectively, may well be used in analytical instrument systems wherein non-polarized light intensity is of interest. In particular, these electro-optical channels can be effectively utilized to measure changes in transmitted light intensities caused by the associated chemical reaction processes employed in coagulation and chromogenic instrumentation. It is therefore to be understood that various changes in the details, materials steps, and arrangements of parts, which have been described and illustrated to explain the nature of the invention, may be made by those skilled in the art within the principle and scope of the invention as expressed in the appended claims.

I claim:

1. A fluorescence polarization instrument system for measurement of the content and concentration of a sample of body fluid treated with a selected fluorescent dye, comprising:
light generating means for projecting a linearly polarized beam of excitation light incident to the sample;
optical means adapted to receive emitted fluorescence from the sample for transmitting a linearly polarized component thereof;
electro-optical means coupled to receive the linearly polarized component of emitted fluorescence for producing digital data indicative of the intensity thereof, said electro-optical means more specifically comprising compensated converter circuitry employing chopper stabilization to correct automatically for offset currents and temperature drift affecting the production of the digital data; and
micro-computer means connected to receive the digital data for determining the content and concentration of the fluid sample therefrom.

2. The fluorescence polarization instrument system according to claim 1, wherein said electro-optical means further comprises:
photodetector means for producing an analog voltage signal indicative of the intensity of the polarized component of emitted fluorescence;
said compensated converter circuitry being connected to receive the analog voltage signal from said photodetector means for producing a digital frequency signal corrected for offsets and drifts by chopper stabilization of the analog voltage signal received; and a counter connected to receive the digital frequency signal from said converter means for producing digital data indicative of the intensity of the polarized component of emitted fluorescence.

3. The fluorescence polarization instrument system according to claim 2, wherein said compensated converter circuitry comprises:

a voltage-to-frequency converter circuit connected to said photodetector means for converting the analog voltage signal to a digital frequency signal; and a compensation amplifier circuit connected in parallel between said photodetector means and said converter circuit for automatically correcting the digital frequency signal for offsets and drifts affecting the analog voltage signal.

4. The fluorescence polarization instrument system according to claim 3, wherein said voltage-to-frequency converter circuit comprises:

an integrated voltage-to-frequency converter designed to convert analog voltages into digital frequency pulses by means of charge-balancing.

5. The fluorescence polarization instrument system according to claim 3, wherein said compensation amplifier circuit comprises:

an integrated operational amplifier chopper-stabilized to produce a continuous output signal despite random changes in input offset voltages to said amplifier.

6. The fluorescence polarization instrument system according to claim 2, wherein said optical means comprises:

an optical filter positioned to receive the emitted fluorescence and having a bandwidth selected in accordance with the absorption spectrum of the flourescent dye; and a film polarizer optically connected to said filter and oriented to pass a linearly polarized component of the emitted flourescence therefrom to said electro-optical means.

7. The fluorescence polarization instrument system according to claim 6 wherein said light generating means comprises:

a broad-band light source;

a collimator lens optically connected to said light source; and an optical filter coupled to receive light from said collimator lens and having a bandwidth limited to correspond with the absorption peak of the selected flourescent dye.

8. The fluorescence polarization instrument system according to claim 7, further comprising:

display means connected to said micro-computer means for reporting the content and concentration of the fluid sample.

9. An electro-optical system for measuring the level of light intensity projected through a fluid sample chemically treated to promote a reaction process analytic thereof, comprising:

photodetector means for producing an analog voltage signal indicative of the intensity of the projected light;

compensated converter means connected to receive the analog voltage signal from said photodetector means for producing a digital frequency signal corrected for offsets and drifts by chopper stabilization of the analog voltage signal received; and counter means connected to receive the digital frequency signal from said converter means for producing digital data indicative of the light intensity.

10. The electro-optical measuring system according to claim 9, wherein said compensated converter means comprises:

a voltage-to-frequency converter circuit connected to said photodetector means for converting the analog voltage signal to a digital frequency signal; and a compensation amplifier circuit connected in parallel between said photodetector means and said converter circuit for automatically correcting the digital frequency signal for offsets and drifts affecting the analog voltage signal.

11. The electro-optical measuring system according to claim 10, wherein said voltage-to-frequency converter circuit comprises:

an integrated voltage-to-frequency converter designed to convert analog voltages into digital frequency pulses by means of charge-balancing.

12. The electro-optical measuring system according to claim 11, wherein said compensation amplifier circuit comprises:

an integrated operational amplifier chopper-stabilized to produce a continuous output signal despite random changes in input offset voltages to said amplifier.

13. The electro-optical measuring system according to claim 10, further comprising:

micro-computer means connected to receive the digital data for determining the content and concentration of the fluid sample therefrom; and display means connected to said micro-computer means for reporting the content and concentration of the fluid sample.

14. In a fluorescence polarization instrument system of the type used to analyze the content and concentration of a sample of body fluid by measuring the level of polarized fluorescence emitted by the fluid sample following treatment with a selected fluorescent dye and excitation by a selected bandwidth of polarized light, the improvement comprising:

photodetector means for producing an analog voltage signal indicative of the intensity of the emitted polarized fluorescence;

converter means coupled to said photodetector means for converting the analog voltage signal to a digital frequency signal;

compensation amplifier means coupled between said photodetector means and said converter means for stabilizing the analog voltage signal; and counter means connected to receive the digital frequency signal from said converter means for producing digital date indicative of the intensity of the emitted polarized fluorescence.

15. The improvement according to claim 14, wherein said converter means comprises:

a voltage-to-frequency converter circuit connected to said photodetector means for converting the analog voltage signal to a digital frequency signal.

16. The improvement according to claim 15, wherein said converter circuit comprises:

an integrated voltage-to-frequency converter designed to convert analog voltages into digital frequency pulses by means of charge-balancing.

17. The improvement according to claim 14, wherein said compensation amplifier means comprises:
a compensation amplifier circuit connected in parallel between said photodetector means and said converter means for automatically correcting the digital frequency signal for offsets and drifts affecting the analog voltage signal.

18. The improvement according to claim 17, wherein said compensation amplifier circuit comprises:
an integrated operational amplifier chopper-stabilized to produce a continuous output signal despite random changes in input offset voltages to said amplifier.

* * * * *